(12) United States Patent
Randall

(10) Patent No.: US 10,806,476 B2
(45) Date of Patent: Oct. 20, 2020

(54) ANTERIOR—POSTERIOR INFLATABLE NOSEBLEED PACKING

(71) Applicant: David Awrey Randall, Springfield, MO (US)

(72) Inventor: David Awrey Randall, Springfield, MO (US)

(*) Notice: Subject to any disclaimer, the term of this patent is extended or adjusted under 35 U.S.C. 154(b) by 178 days.

(21) Appl. No.: 15/810,087

(22) Filed: Nov. 12, 2017

(65) Prior Publication Data

US 2019/0142446 A1 May 16, 2019

(51) Int. Cl.
*A61B 17/24* (2006.01)
*A61B 17/12* (2006.01)

(52) U.S. Cl.
CPC ........ *A61B 17/24* (2013.01); *A61B 17/12104* (2013.01); *A61B 17/12136* (2013.01); *A61M 2210/0618* (2013.01)

(58) Field of Classification Search
CPC .............. A61B 17/24; A61B 17/12104; A61B 17/12136; A61M 2210/0618
USPC ..................... 606/196, 199; 604/101.01, 514
See application file for complete search history.

(56) References Cited

U.S. PATENT DOCUMENTS

| | | | |
|---|---|---|---|
| 1,051,850 A | 1/1913 | Sandmark |
| 1,235,095 A | 7/1917 | Beck |
| 1,690,995 A | 11/1928 | Pratt |
| 1,732,697 A | 10/1929 | Ryan |
| 2,179,964 A | 11/1939 | Stevens |
| 2,215,126 A | 9/1940 | McMillin |
| 2,265,387 A | 12/1941 | McMillin |
| 2,335,936 A | 12/1943 | Hanlon |
| 2,493,326 A | 1/1950 | Trinder |
| 2,638,093 A | 5/1953 | Kulick |
| 2,647,515 A | 8/1953 | Pollock et al. |
| 2,691,985 A | 10/1954 | Newsom |
| 2,847,997 A | 8/1958 | Tibone |
| 3,045,677 A | 7/1962 | Wallace |
| 3,049,125 A | 8/1962 | Kriwkowitsch |
| 3,154,077 A | 10/1964 | Cannon |
| 3,420,237 A | 1/1969 | Fortay |
| 3,516,407 A | 6/1970 | Ruggero |
| 3,570,494 A | 3/1971 | Gottschalk |
| 3,766,924 A | 10/1973 | Pidgeon |

(Continued)

OTHER PUBLICATIONS

Gidoll, Sidney H., "An Improved Packing for Septum Resections Permitting Nasal Respiration", Archives of Otolaryngology, 1935, 2 pgs., 8:466-7.

(Continued)

*Primary Examiner* — Vy Q Bui

(74) *Attorney, Agent, or Firm* — Thomas M. Freidburger

(57) ABSTRACT

A method using one or two inflatable balloon packs for the treatment of epistaxis (nosebleed) from any internal area of the nose. The balloon packing is adapted to be received in and apply pressure to all aspects of the nasal cavity on inflation with a suitable fluid. The anterior (forward) balloon packing has a channel extending between its front and rear aspects to allow passage of a second, posterior (rearward) balloon packing; said posterior packing is adapted to apply pressure to the nasopharynx upon inflation with a suitable fluid. Said method has a means of tensioning packing to continuously apply pressure necessary to control bleeding.

9 Claims, 10 Drawing Sheets

(56) References Cited

U.S. PATENT DOCUMENTS

Figure 1A:
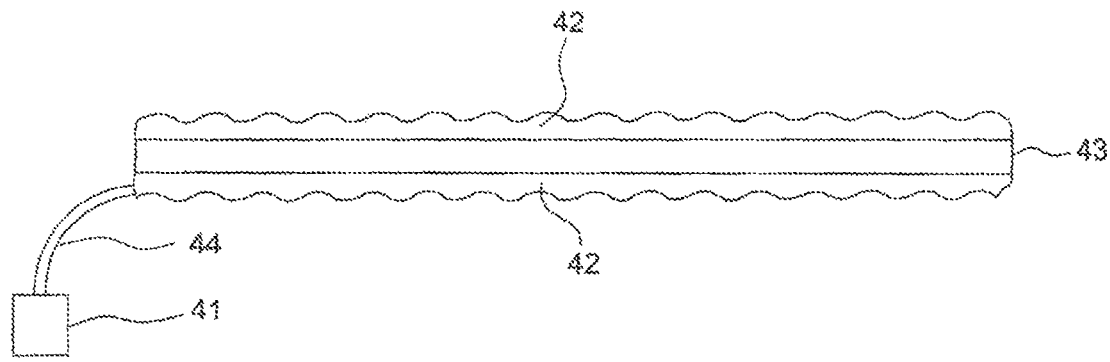

| | | |
|---|---|---|
| 3,884,241 A | 5/1975 | Walker |
| 3,903,893 A | 9/1975 | Scheer |
| 3,935,859 A | 2/1976 | Doyle |
| 4,030,504 A | 6/1977 | Doyle |
| 4,102,342 A | 7/1978 | Akiyama et al. |
| 4,338,941 A | 7/1982 | Payton |
| 4,568,326 A | 2/1986 | Rangaswamy |
| 4,592,357 A | 6/1986 | Ersek |
| 4,606,346 A | 8/1986 | Berg et al. |
| 4,646,739 A | 3/1987 | Doyle |
| 4,820,266 A | 4/1989 | Berry |
| 4,883,465 A | 11/1989 | Brennan |
| 4,950,280 A | 8/1990 | Brennan |
| 5,011,474 A | 4/1991 | Brennan |
| 5,024,658 A | 6/1991 | Kozlov |
| 5,139,510 A | 8/1992 | Goldsmith, III et al. |
| 5,336,163 A | 8/1994 | DeMane et al. |
| 5,383,891 A | 1/1995 | Walker |
| 5,391,179 A | 2/1995 | Mezzoli |
| 5,454,817 A | 10/1995 | Katz |
| 5,546,964 A | 8/1996 | Stangerup |
| 5,584,822 A | 12/1996 | Lively et al. |
| 5,584,827 A | 12/1996 | Korteweg et al. |
| 5,588,965 A | 12/1996 | Burton et al. |
| 5,755,706 A | 5/1998 | Kronenthal et al. |
| 5,827,224 A | 10/1998 | Shippert |
| D406,888 S | 3/1999 | Doyle |
| D406,890 S | 3/1999 | Doyle |
| 5,899,918 A | 5/1999 | Knott et al. |
| 6,027,478 A | 2/2000 | Katz |
| 6,123,697 A | 9/2000 | Shipped |
| 6,183,436 B1 | 2/2001 | Korteweg et al. |
| 6,306,154 B1 | 10/2001 | Hudson et al. |
| 6,607,546 B1 | 8/2003 | Murken |
| 6,669,711 B1 | 12/2003 | Noda |
| 6,768,040 B1 | 7/2004 | Sessions et al. |
| 7,108,706 B2 | 9/2006 | Hogle |
| 7,294,138 B2 | 11/2007 | Shippert |
| 7,695,490 B2 | 4/2010 | Hogle |
| 7,727,186 B2 | 6/2010 | Makower et al. |
| 7,909,845 B2 | 3/2011 | Ashenhurst |
| 8,137,375 B2 | 3/2012 | Hudson et al. |
| 8,974,486 B2 | 3/2015 | Kotler |
| 2002/0077653 A1 | 6/2002 | Hudson et al. |
| 2003/0105483 A1 | 6/2003 | Hudson et al. |
| 2003/0236547 A2 | 12/2003 | Hudson et al. |
| 2004/0194788 A1 | 10/2004 | Sweet |
| 2006/0095066 A1* | 5/2006 | Chang et al. .......... 606/199 |

OTHER PUBLICATIONS

Stevens, R.W., "Improved Intranasal Packing—A Rubber Pneumatic Pack", Archives of Otolaryngology, 1936, 4 pgs., 23:232-5.

Printout from website mckesson.com, Beaver-Visitec International, ULTRACELL, 3 pgs., Medline, Northfield, IL.

Printout from website medline.com, Merocel Standard Nasal Packing by Medtronic, 2 pgs., Medtronic, Minneapolis, MN.

Printout from website bosmed.com, RHINOCELL Sinus Packing, 3 pgs., Boston Medical, Shrewsbury, MA.

Printout from website shippertmedical.com, Shippert Rhino Rocket, 8 pgs., Medline, Northfield, IL.

Printout from website rapidrhino.com, Rapid Rhino Epistaxis Products, 7 pgs., Smith & Nephew, London, UK.

Printout from website medline.com, Epistat Nasal Catheter by Xomed-Treace, 2 pgs., Medtronic, Minneapolis, MN.

Bivona Double Balloon Epistaxis Catheter, 1 pg., Smiths Medical, Minneapolis, MN.

* cited by examiner

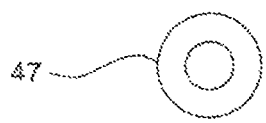
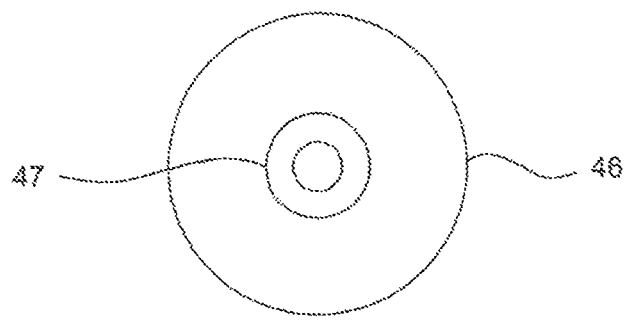
FIG. 8A  FIG. 8B
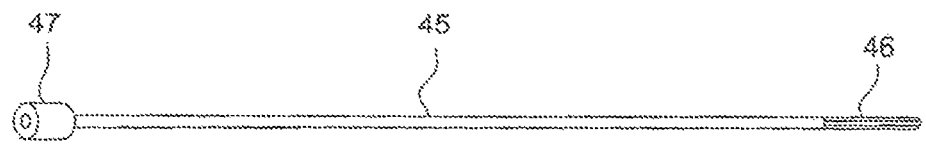
FIG. 9
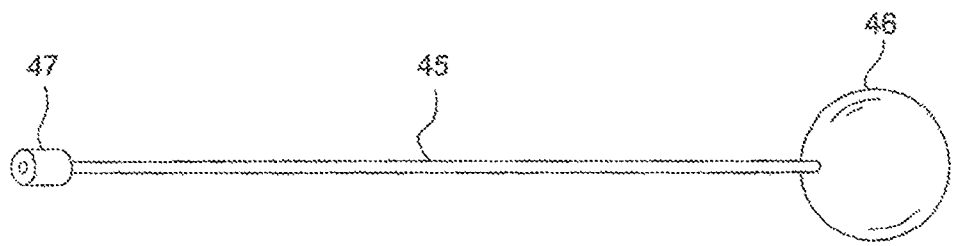
FIG. 10

ANTERIOR—POSTERIOR INFLATABLE NOSEBLEED PACKING

CROSS REFERENCE TO RELATED APPLICATIONS

This application claims the benefits of provisional patent application Ser. No. 62/299,625 filed Feb. 25, 2016.

TECHNICAL FIELD

The present invention relates to systems, methods and apparatus for the control of nosebleed (epistaxis), and more particularly to medical devices that are inserted into the nose to control epistaxis that may occur at the anterior (front) and/or posterior (back) of the nasal cavity.

INTERNATIONAL CLASSIFICATION

| | | |
|---|---|---|
| A61M 29/00 | (2006.01) | |
| A61M 31/00 | (2006.01) | |
| A61M 1/00 | (2006.01) | |
| A61F 13/20 | (2006.01) | |
| A61F 5/44 | (2006.01) | |

UNITED STATES CLASSIFICATION

606/199, 128/207, 604/11, 604/104, 604/286, 604/328, 604/358, 604/540, 640/904, 604/907, 604/913, 606/162, 606/196

FIELD OF CLASSIFICATION SEARCH

128/206, 128/358, 604/1, 604/11, 604/104, 604/285, 604/540, 604/327, 604/328, 604/358, 604/369, 604/385, 604/904, 604/907, 604/913, 606/191, 606/129, 606/196, 606/199, 606/162

REFERENCES CITED

| | | |
|---|---|---|
| 1913 | 1,051,850 | Sandmark |
| 1917 | 1,235,095 | Beck |
| 1928 | 1,690,995 | Pratt |
| 1929 | 1,732,697 | Ryan |
| 1935 | | Giddol S. An improved method for packing septum resections permitting nasal respiration. *Archives of Otolaryngology.* 1935; 8: 466-7 |
| 1936 | | Stevens R. Improved nasal packing. *Archives of Otolaryngology.* 1936; 23: 232-5 |
| 1939 | 2,179,964 | Stevens |
| 1940 | 2,215,126 | McMillin |
| 1941 | 2,265,387 | McMillin |
| 1943 | 2,335,936 | Hanlon |
| 1950 | 2,493,326 | Trinder |
| 1953 | 2,638,993 | Kulick |
| 1953 | 2,647,515 | Pollock |
| 1954 | 2,691,985 | Newsom |
| 1958 | 2,847,997 | Tibone |
| 1960 | 3,045,677 | Walker |
| 1962 | 3,049,125 | Kriwkowitsch |
| 1964 | 3,154,077 | Cannon |
| 1968 | 3,570,494 | Gottschalk |
| 1969 | 3,420,327 | Fortay |
| 1970 | 3,516,407 | Ruggero |
| 1973 | 3,766,924 | Pidgeon |
| 1975 | 3,884,241 | Walker |
| 1975 | 3,903,893 | Scheer |
| 1976 | 3,935,859 | Doyle |
| 1977 | 4,030,504 | Doyle |
| 1978 | 4,102,342 | Akiyama |
| 1982 | 4,338,941 | Payton |
| 1986 | 4,568,326 | Rangaswamy |
| 1986 | 4,592,357 | Ersek |
| 1986 | 4,606,346 | Berg |
| 1987 | 4,646,739 | Doyle |
| 1989 | 4,820,266 | Berry |
| 1989 | 4,883,465 | Brennan |
| 1990 | 4,950,280 | Brennan |
| 1991 | 5,024,65 | Kozlov |
| 1991 | 5,011,474 | Brennan |
| 1992 | 5,139,510 | Goldsmith |
| 1994 | 5,336,163 | DeMane |
| 1995 | 5,391,179 | Mezzoli |
| 1995 | 5,383,891 | Walker |
| 1995 | 5,454,817 | Katz |
| 1996 | 5,546,964 | Stangerup |
| 1996 | 5,584,822 | Lively |
| 1996 | 5,584,827 | Korteweg |
| 1996 | 5,588,965 | Burton |
| 1998 | 5,755,706 | Kronenthal |
| 1998 | 5,827,224 | Shippert |
| 1999 | D406,888 | Doyle |
| 1999 | D406,890 | Doyle |
| 1999 | 4,899,918 | Knott |
| 2000 | 6,027,478 | Katz |
| 2000 | 6,123,697 | Shippert |
| 2001 | 6,306,154 B1 | Hudson |
| 2001 | 6,183,436 B1 | Korteweg |
| 2003 | 6,669,711 B1 | Noda |
| 2002 | 2002/0077653 A1 | Hudson |
| 2003 | 2003/0105483 A1 | Hudson |
| 2003 | 2003/0236547 A2 | Hudson |
| 2003 | 6,607,546 B1 | Murken |
| 2004 | 6,768,040 B1 | Sessions |
| 2004 | 2004/0194788 A1 | Sweet |
| 2006 | 7,108,706 B2 | Hogle |
| 2007 | 7,294,138 B2 | Shippert |
| 2010 | 7,695,490 B2 | Hogle |
| 2010 | 7,727,186 B2 | Makower |
| 2011 | 7,909,845 B2 | Ashenhurst |
| 2012 | 8,137,375 B2 | Hudson |
| 2015 | 8,974,486 B2 | Knotler |

Commercially Available Sponge Packs
Beaver—Visitec Ultracell® (Medline, Northfield, Ill.)
Merocel® (Medtronic, Minneapolis, Minn.)
Rhinocell® (Boston Medical, Shrewsbury, Mass.)
Shippert Rhino Rocket® (Medline, Northfield, Ill.)
Commercially Available Inflatable Packs
Rapid Rhino® (Smith & Nephew London, UK)
Epistat® (Medtronic, Minneapolis, Minn.)
Bivona® (Smiths Medical Minneapolis, Minn.)

BACKGROUND OF INVENTION

Epistaxis (nosebleed) remains a common problem. This often requires treatment in emergency department and urgent care settings. Ninety percent of nosebleeds originate from the anterior (frontal) nasal cavity while a minority begin posteriorly (back of the nose). Some situations allow identification of a specific bleeding site whose blood vessel(s) can be sealed shut with cautery (application of chemical or by heating means such as electrosurgical devices or LASERs). In many other cases, the physician finds no specific source and must resort to the application of pressure on the presumed site by placing packing into the nose in order to stop bleeding.

Traditional Anterior Nasal Packing

Traditional nasal packing involves layering a long strip of cloth gauze horizontally in alternating backward and forward directions in the nose, beginning along the nasal floor and then stacking progressively upward to fill the nasal cavity. This technique requires a certain amount of expertise and technical skill. Correct gauze positioning often presents a daunting challenge for urgent care or emergency department physicians who perform this procedure infrequently. As a practical matter, placement by an inexperienced provider prolongs the time required to control epistaxis which increases the already significant patient discomfort associated with any packing and, likely, impairs the actual success of treatment. Further, failure of (or unfamiliarity with) this method then requires consultation with an otolaryngologist (ear, nose, and throat specialist), which incurs additional cost and treatment time. The patient typically then undergoes placement of a different nasal pack with its attendant pain and nasal mucosal trauma. Need exists for means to allow the non-otolaryngologist to control nosebleeds quickly and easily with minimal patient discomfort This has prompted the search for an effective, simple, and less painful means of controlling nosebleed. The plethora of designs testifies to the fact that an optimal solution remains elusive. Existing devices and patents will be discussed both in a general sense and also with reference to the prior art.

Traditional Posterior Nasal Packing

Unlike anterior packing (which usually remains in place once positioned) the anatomy of the choana (posterior nasal opening) and the nasopharynx immediately behind it requires that that a forward pull must be maintained on the pack to keep in in place and apply necessary pressure. Otherwise, it will simply dislodge backward and downward, offering no benefit yet incurring risk of falling into the laryngeal area and causing airway obstruction. A variety of absorbent materials such as cotton gauze, wool, and even part of a vaginal tampon has been employed. These require a string or other means of forward traction to hold the pack snugly in the posterior choana. The physician typically places these through the mouth, lodges them above the soft palate at the choana, and then must bring the strings forward and out the nostril. A third string (used later for pack retrieval) is brought out of the mouth and taped to the cheek. Understandably, this is technically difficult and predictably uncomfortable. Several other designs have been proposed, patented, and/or manufactured to remedy the above issues. Each of these has problems and limitations with regard to effectiveness and ease of use that shall be discussed in the review of prior art.

REVIEW OF PRIOR ART

Non-Expanding Devices

Several devices apply pressure to bleeding site(s) by different methods than the above described more typical nasal packing. An example of one is a nasal clamp that squeezes the external nose and applies internal pressure to bleeding sites. (U.S. Pat. Nos. 5,899,918; 6,666,211 B1) A second involves rigid strips of material that are inserted into the nose to apply pressure. (U.S. Pat. No. 4,820,266) Another has a length of non-expanding material that is pulled forward from the mouth and throat, into the back of the nose on both sides, and brought anteriorly on either side for pressure application. (U.S. Pat. No. 3,420,237) One has quite a different approach, which is to insert a device beneath the upper lip to apply pressure to vessels entering the nasal cavity from below. (2004/0194788 A1; U.S. Pat. No. 9,265,666 B2). In over a quarter century of clinical otolaryngology practice, this inventor has only seen the rare use of an external nasal clamp and never the other devices described in this paragraph.

Absorbent Sponge Devices

A variety of expandable nasal sponge packs has been patented. (U.S. Pat. Nos. 1,732,697; 4,030,504; 4,646,739; 4,950,280; 5,336,163; 5,383,89; 5,584,822; 5,584,827; 5,755,706; 5,827,224; D 406,888; D 406,890; 6,123,697; 6,183,436 B1; 6,306,154 B1; 6,768,040 B1; 7,294,138 B2; 7,727,186 B2; 7,799,048 B2; 7,909,845 B2; 8,137,375 B2) A partial list of commercially available products includes the Merocel®, Ultracel®, Rhinocell®, and Rhino Rocket® epistaxis sponges cited above. They are based somewhat on the function of an absorbent vaginal tampon and have sometimes been referred to as nasal tampons. These are thin, rigid, compressed sponges that are typically a centimeter or more in height, several millimeters in thickness, and range in length from 1-2 centimeters up to about 10 centimeters. A multitude of shapes and sizes has become commercially available. Some are rectangular while others seek to expand upward to more nearly fill the whole of the nasal cavity. After insertion into the nose, they absorb fluid to expand, soften, conform to the nasal cavity, and apply pressure to the bleeding site. Advantages include the simplicity and reliability of design and manufacture. Some incorporate a longitudinal tube of about 4 mm diameter to allow respiration through the packed nasal cavity while the device is in place.

Anterior Nasal Balloon Packing

A balloon device provides an alternative method to the anterior sponge to provide an expandable pack that can apply pressure to a nosebleed site. Many designs have been described. (U.S. Pat. Nos. 1,051,850; 1,235,095; Stevens, *Archives of Otolaryngology.* 1935; U.S. Pat. Nos. 2,197,964; 2,215,126; 2,265,387; 2,647,515; 2,691,985; 3,049,125; 3,516,407; 4,568,326; 4,592,347; 4,606,346; 5,139,150; 2002/0077653 A1; 2003/0105483 A1; 2003/0236547 A1)

Very few inflatable anterior packs have been used in actual clinical service. Rapid Rhino® offers a number of balloon products in varying sizes. These are comprised of an elongated balloon that is encased in a mesh of proprietary carboxymethyl cellulose (CMC) called Gel Knit®. After insertion into the nasal cavity, these are inflated by injection of fluid from a syringe attached to a standard Luer-Lok® type attachment via a thin tube connected to the balloon. The CMC mesh serves two purposes. It becomes very slippery after being wetted to facilitate insertion. The mesh also acts as a topical hemostatic agent to discourage bleeding. The Epistat® and Bivona® double balloon catheters (described below) can be similarly used by inflating only the forward of their two balloons.

Posterior Epistaxis

While the sponge and balloon packs offer fast and relatively easy means to pack an anterior nosebleed, epistaxis from the back of the nose has remained the far greater challenge for the non-otolaryngologist. This requires overcoming several problems:

Difficulty of placement of a pack slightly less than the size of a ping-pong ball behind the back of the nose/nasopharynx.

Necessity of passing strings or other tensile material out the nostril to maintain forward pull on the pack as well as to bring a separate retrieval string out through the mouth (taped to the cheek) for effective pack removal.

Infrequent practice understandably causes unfamiliarity with this technique. This may cause unsatisfactory results and subsequent need for consultation with an ear, nose, and throat specialist. Associated with this are increased treatment time in the care facility, additional pain/trauma with repeated packing attempts, plus the added cost of the otolaryngology consultation. Finally, these treatment settings usually lack many of the necessary supplies necessary for traditional anterior-posterior packing.

Posterior Nasal Packs

Several devices have been patented specifically for packing the back of the nose. (U.S. Pat. Nos. 2,847,997; 4,102,342; 4,338,941; 5,546,964; 6,027,478; 2003 6,669,711 B1; 7,727,186 B2) These include both inflatable as well as solid designs. None are presently in production, perhaps due to their impractical nature.

Anterior Posterior Sponge Packing

Review of existing patents yielded no sponge device intended solely for the back of the nasal cavity. One device incorporates both anterior and posterior sponges. (U.S. Pat. No. 5,383,891) Two patents exist for a combination design with an anterior sponge and posterior balloon pack. (U.S. Pat. Nos. 4,883,465; 5,011,474) None are available for medical use.

Anterior Posterior Balloon Packing

Various patents have been granted for designs with inflatable balloons that apply pressure at both the front and back of the nose (U.S. Pat. Nos. 2,493,326; 3,570,494; 3,766,928; 3,903,893; 6,607,546 B1; 7,108,706 B2; 7,695,490 B2; Epistat® (Medtronic, Minneapolis, Minn.); Bivona® (Smiths Medical Minneapolis, Minn.); Rapid Rhino® 900 (Smith & Nephew London, UK)) The 2006 and 2010 designs by Hogle (U.S. Pat. No. 7,108,706 B2, 7,695,490 B2) use a pair of soft, non-elastic balloons to provide more even pressure throughout the nasal cavity. The 2003 Murken patent (U.S. Pat. No. 6,607,546 B1) incorporates various types of protrusions in its different embodiments. These seek to reach into recesses of the nasal cavity (such as underneath turbinates) to better apply pressure although greatly increase complexity of manufacture. Below are several packs that are currently available.

Commercially Available Anterior-Posterior Double Balloon Nasal Catheters

Several products have been created to facilitate ease of placing a catheter that treats anterior and posterior epistaxis. Probably the most commonly used of these is a double balloon nasal catheter. Essentially identical designs are manufactured by Bivona® and as the Medtronic® Epistat®. Each has a 30-milliliter balloon for the anterior nasal cavity and a 10-milliliter balloon at the end opposite the inflation port to occlude the posterior nasal cavity and choana. The physician passes the catheter to the back of the nose and then inflates two balloons to the extent necessary to treat the nosebleed. Rapid Rhino® model RR 900 provides a 9-centimeter pack which similarly has separate anterior and separate posterior balloon encased in the carboxymethyl cellulose mesh. It is inflated in a similar manner to the Epistat® and Bivona®.

Disadvantages of Prior Art Nasal Packs

The above designs offer many advantages in comparison to traditional anterior-posterior packing. Need exists, however, for a reliable method for the non-specialist to easily transition from anterior to anterior/posterior packing when the former fails. Drawbacks of existing prior art are reviewed below.

Disadvantages of Rigid Sponge Packing

Despite the simplicity of design and general ease of use, these devices have a number of drawbacks in clinical use:

They are rigid, hard, and non-yielding. Insertion into nasal cavities of varying shape can result in significant pain as well as abrasions and tears of the nasal mucosa that may result in additional hemorrhage.

On occasion, a nasal septal deviation or other anatomic variant can completely prevent insertion of one of these rigid devices.

Some sponges incorporate longitudinal tubes purportedly to allow respiration. Unfortunately, they greatly increase the width of the device and cause additional difficulty, trauma, and pain with insertion. However, the effective airflow through a 3-4 mm tube seems dubious, particularly when it becomes occluded with mucus and blood.

These sponge devices absorb blood thereby offer culture media for bacteria. Toxic shock syndrome has occurred in this type of device in a similar manner to vaginal tampons.

The surfaces of these sponge devices often adhere to the mucosa and, with removal, can disrupt the healing surface and cause re-bleeding.

Disadvantages of Anterior Balloon Packing

These offer enhanced comfort for patients and ease of insertion by physicians. Limitations with their use include:

Provide treatment of anterior nosebleeds only.

Transition to anterior-posterior packing results in extra cost when the anterior pack is used, fails, and is discarded.

Many incorporate elastic balloons that concentrate pressure at their center, which usually corresponds to the middle of the nasal cavity and away from anterior sites where bleeding predominates. This balloon shape may require higher inflation pressure, exacerbating pain.

None exists as part of a system that includes a simple method of adding posterior packing to the already in-place anterior pack.

General Disadvantages of Anterior-Posterior Balloon Packing

The packs described below are systems generally intended packing both the front and back of the nose. In addition to drawbacks described more fully below, they share some common disadvantages:

Typically, they are used when an anterior pack has failed and been discarded. This waste increases treatment cost.

These are all one-size-fits-all devices and may not fit varying anatomic dimensions of different patients. The two balloons cannot be positioned and tensioned separately.

They lack means to keep the pack in a specific anterior-posterior orientation to the nasal cavity. They can slip out of position which compromises their effectiveness.

Certain of the designs could be used for anterior-only packing and then have the posterior balloon inflated if needed. However, that would increase cost by using a more complicated and expensive pack for every nosebleed.

Particular problems associated with the various designs are described below.

Bivona® and Epistat® Catheters

These devices seek to offer a simplified means to pack the front and the back of the nose. Some issues arise with clinical use:

Both incorporate a fairly rigid shaft with an interior lumen preventing passage through narrow nasal cavities while offering minimal airflow.

They have elastic balloons with the attendant problems noted above.

These can migrate posteriorly. The Y-shaped external end can apply pressure to the nostril margins resulting in tissue loss and permanent notching defects.

Trinder (U.S. Pat. No. 2,493,326)

This device shares issues similar to the Bivona® and Epistat®.

Gottschalk (U.S. Pat. No. 3,570,494)

This also has similar disadvantages to the Bivona® and Epistat® devices as described below although it lacks the Y-shaped inflation portion and its associated problems.

The forward balloon actually inflates in the nasal opening. This increases the potential for discomfort as well as for damage to the functionally and cosmetically important nostril.

Pidgeon (U.S. Pat. No. 3,766,928)

The pair of small balloons only provide occlusion of the front and rear of the nasal cavity.

They lack means to apply hemostatic pressure or potential application of a hemostatic agent throughout the rest of the nasal cavity The pack appears to be particularly susceptible to migration out of position.

Scheer U.S. Pat. No. 3,903,893

Drawbacks as described for Pidgeon, above.

Larger diameter shaft of balloon which would make placement problematic with septal deviation or narrow nasal cavities.

Brennan (U.S. Pat. Nos. 4,883,465; 5,011,474)

These two patents incorporate an anterior sponge pack and a posterior balloon pack. Drawbacks include:

Potential difficulty in passing the rigid sponge pack and larger diameter shaft through some noses.

Additional sponge-related problems such as potential for toxic shock and adherence to mucus membrane and chance for re-starting hemorrhage Potential for rearward dislodgement of the device.

Mezzo (U.S. Pat. No. 5,391,179)

This inventor describes several separate designs for anterior and posterior packing. Drawbacks of the designs include:

The preferred embodiment may incorporate a larger diameter core (part #2) for respiration, passage of a nasogastric tube, etc. that may make placement through narrow nasal cavities problematic.

The posterior catheter lacks means to secure it in position

This is not an integrated system for providing combination anterior/posterior packing to address situations when anterior packing alone fails.

Murken U.S. Pat. No. 6,607,546 B1

The various different embodiments incorporate various inflatable protrusions that extend from the main balloon body to better fit the nose and reach into areas that would not normally be addressed by a typical pack. Problems for these include:

Complexity of manufacture to include the numerous protrusions in comparison to a more basic balloon Several of the designs appear difficult to place in the nose Some have larger diameter tubes that may make insertion difficult.

Hogle (U.S. Pat. Nos. 7,108,706 B2; 7,695,490 B2)

These devices seek to address some of the above drawbacks. They feature inelastic balloons in order to better fill the nasal cavity with even pressure while conforming to its irregular shape. It thereby avoids the problem of an elastic balloon, as in the Bivona® Epistat® products that have higher volumes and pressure (hence more pain) in the central part of the balloon cavity. Several drawbacks may be identified with this design, however:

The device length and shape may result in contact with adenoid area and/or soft palate which could cause irritation, pain, and bleeding.

The hollow respiration tube would likely experience obstruction with secretions as mentioned above.

Makower (U.S. Pat. No. 7,727,186 B2)

This patent incorporates a multitude of different catheter designs indicated to diagnose and treat sinusitis as well as other nasal disorders. These functions include irrigation of the nose and sinuses, dilation of stenotic areas, dilating the eustachian tube.

Many appear of questionable patient comfort as well as functionality with regard to placing and maintaining position during use.

None provides good nasal mucosal compression for epistaxis.

Rapid Rhino® 900

This device shares limitations noted above with the Epistat® and Bivona® packs though lacks the Y-shaped portion that can cause tissue damage Although the carboxymethyl cellulose makes the pack slippery to improve ease of insertion, this same quality could make posterior migration more likely.

Origin of Design of this Present Patent

As can be seen, need exists for a simple, easy-to-use, and more comfortable means of placing packing in the nose to treat epistaxis from any site. The desired alternative to the existing designs should incorporate the following attributes:

Ease of use by physicians who lack familiarity with traditional anterior-posterior packing methods.

Emphasis on increased patient comfort. Personal clinical experience for this inventor has demonstrated the pain associated with nasal packing which is only made worse by repeated attempts.

Ability to treat the majority of nosebleeds that occur in the front of the nasal cavity.

Ease of transition to incorporate posterior packing in a simple manner without the cost of discarding the original, failed pack while avoiding the additional treatment time and discomfort of removing that first pack and changing to a second device Reduced cost of a simple anterior balloon design that will treat ninety percent of nosebleeds.

Non-elastic balloons which distribute pressure in the nasal cavity more easily for reduced pain and increased effectiveness.

Option for coating with hemostatic material.

LEGEND OF PARTS

41. Connection for standard medical syringe similar to Luer-Lok® design
42. Anterior catheter balloon.
43. Soft, flexible, and small-diameter tube/lumen running internally along the below the axial center along the length of balloon (42).
44. Inflation tube connecting syringe connector (41) to anterior catheter balloon (42).
45. Shaft of posterior catheter balloon.
46. Balloon at distal end of posterior catheter (45).
47. Connection for standard medical syringe identical to part 41.

48. Hinged or other type of clamp intended to be placed around posterior balloon shaft (45) to secure it in place against bolster (49).
49. Bolster of sponge or other suitable material to pad and protect the nostril from pressure applied by clamp (48).
51. Frontal sinus.
52. Anterior external nose.
53. Nasal cavity.
54. Nostril.
55. Palate.
56. Lower, middle, and upper nasal turbinates.
57. Roof of nasal cavity (anterior skull base).
58. Sphenoid sinus.
59. Nasopharynx/posterior nasal cavity.

LIST OF FIGURES

FIG. 1A. Lateral view of anterior nasal catheter with balloon deflated, ready for insertion into nasal cavity.

Figure 1B:
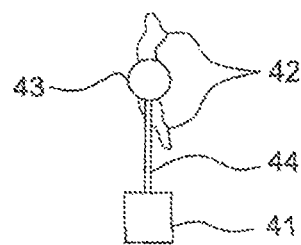

FIG. 1B. End-on view of anterior catheter described in FIG. 1A.

Figure 2A:
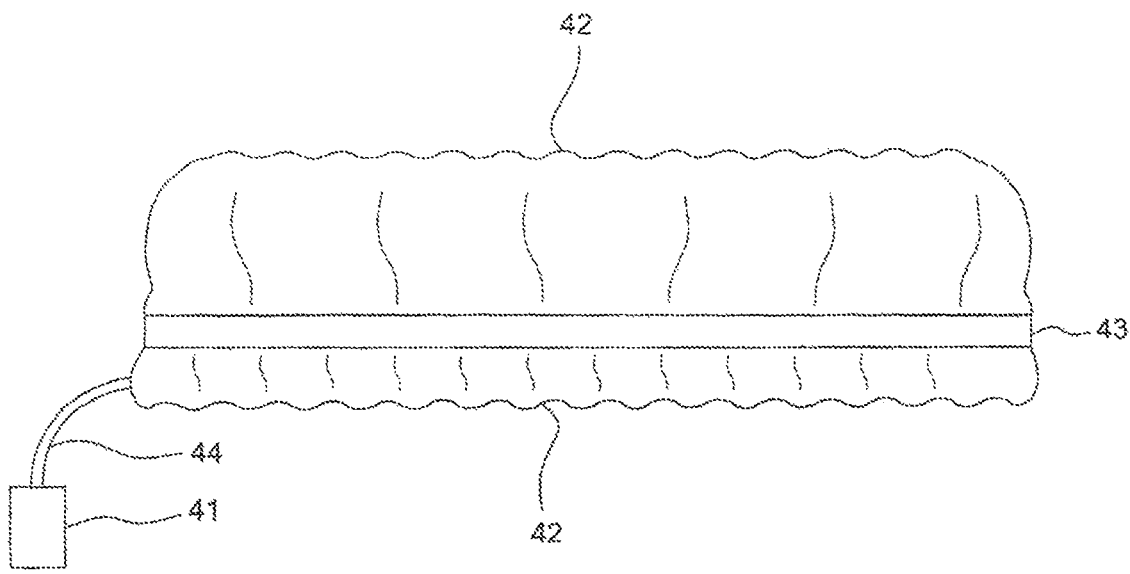

FIG. 2A. Lateral view of anterior nasal catheter with balloon deflated but stretched flat to demonstrate vertical dimension.

Figure 2B:
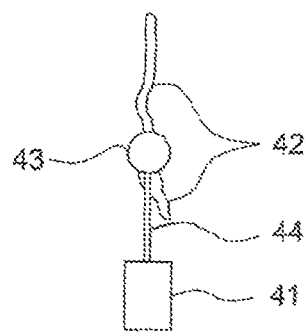

FIG. 2B End-on view of anterior catheter as described in FIG. 2A.

Figure 3A:
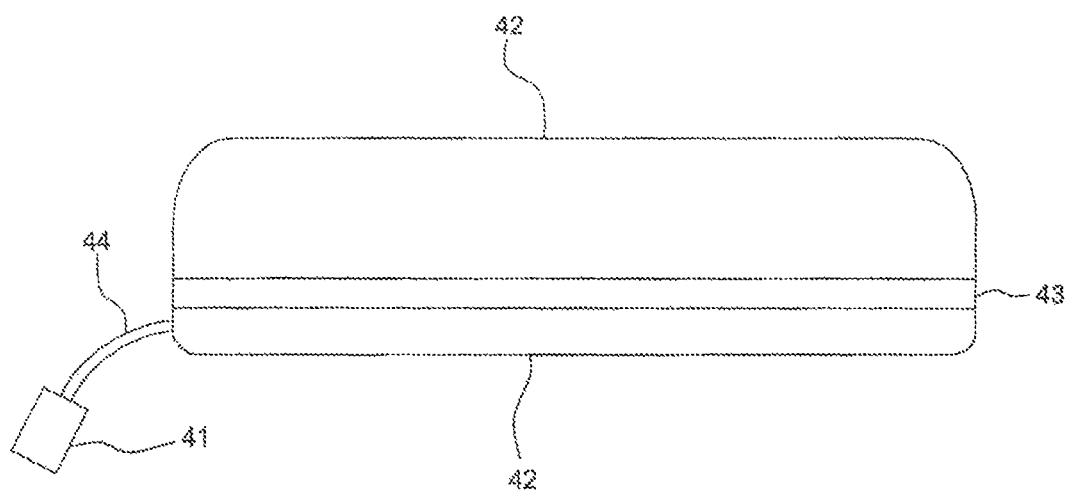

FIG. 3A Lateral view of anterior catheter, inflated.

Figure 3B:
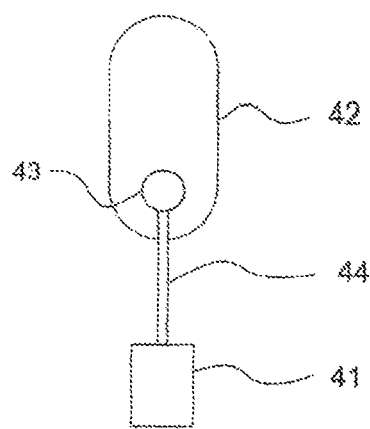

FIG. 3B End-on view of anterior catheter as described in FIG. 3A.

Figure 4:
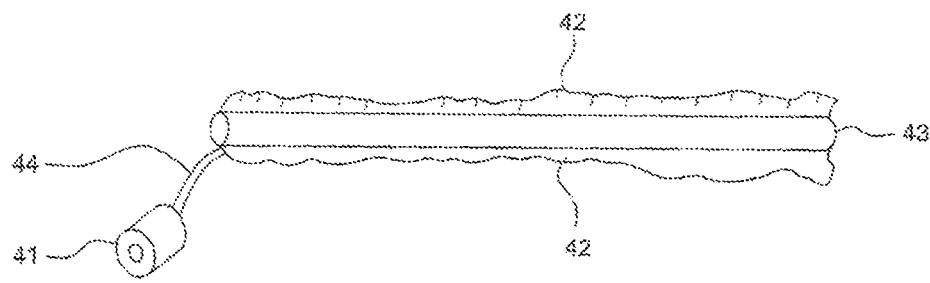

FIG. 4 Three-dimensional view of deflated anterior catheter.

Figure 5:
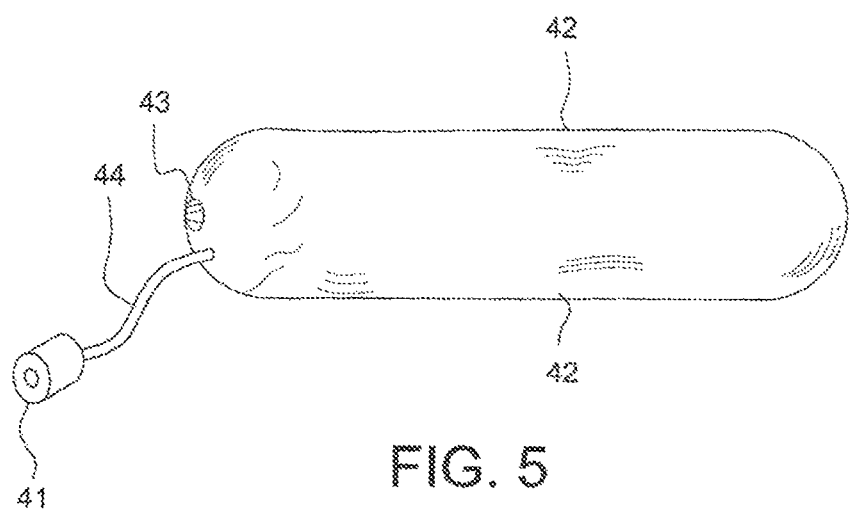

FIG. 5 Three-dimensional view of inflated anterior catheter.

Figure 6:
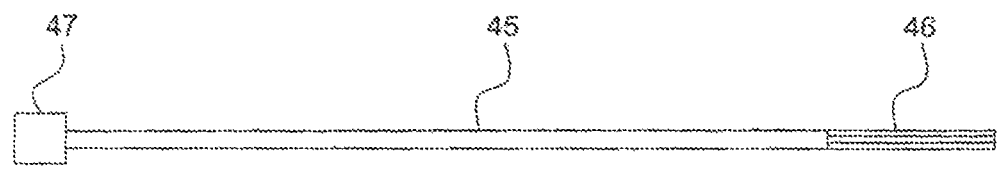

FIG. 6 Lateral view of deflated posterior catheter

Figure 7:
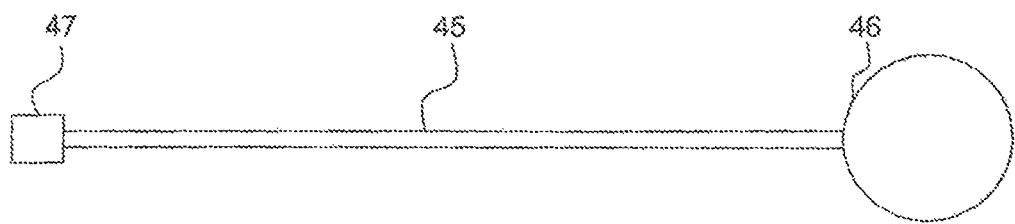

FIG. 7 Lateral view of inflated posterior catheter.

FIG. 8A End-on view of deflated posterior catheter demonstrating the Luer-Lok® type connector to attach to standard medical syringe.

FIG. 8B End-on view of inflated posterior catheter demonstrating the Luer-Lok® type connector to attach to standard medical syringe.

FIG. 9 Three-dimensional view of deflated posterior catheter.

FIG. 10 Three-dimensional view of inflated posterior catheter.

Figure 11A:
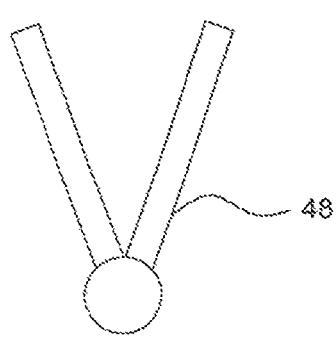

FIG. 11A End-on view of clamping device (48) open.

Figure 11B:
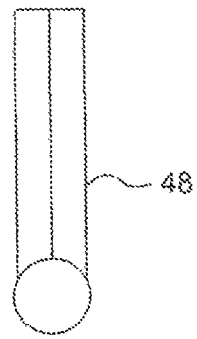

FIG. 11B End-on view of clamping device (48), closed.

Figure 11C:
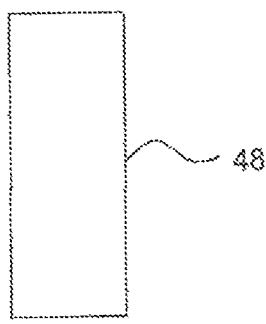

FIG. 11C Lateral view of clamping device (48).

Figure 11D:
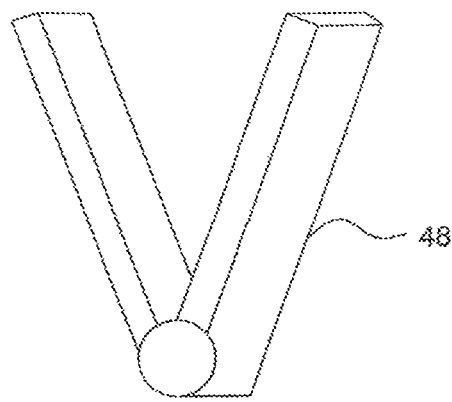

FIG. 11D Three-dimensional view of clamping device (48), open.

Figure 11E:
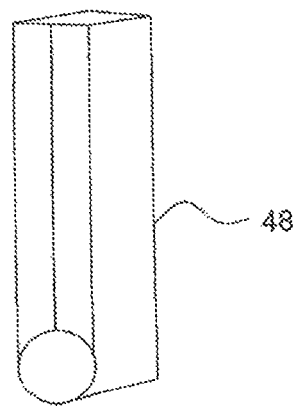

FIG. 11E Three-dimensional view of clamping device (48), closed.

Figure 12A:
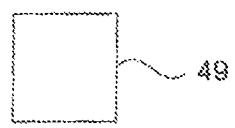

FIG. 12A Lateral view of bolster (49).

Figure 12B:

FIG. 12B End-on view of bolster (49).

Figure 12C:
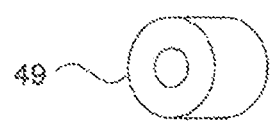

FIG. 12C Three-dimensional view of bolster (49).

Figure 13:
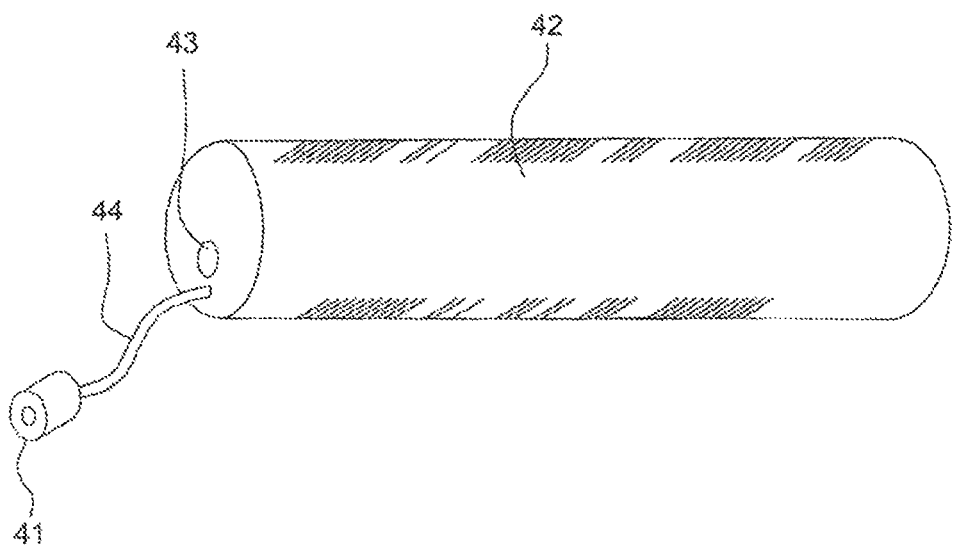

FIG. 13 Three-dimensional view of anterior nasal catheter, inflated.

Figure 14:
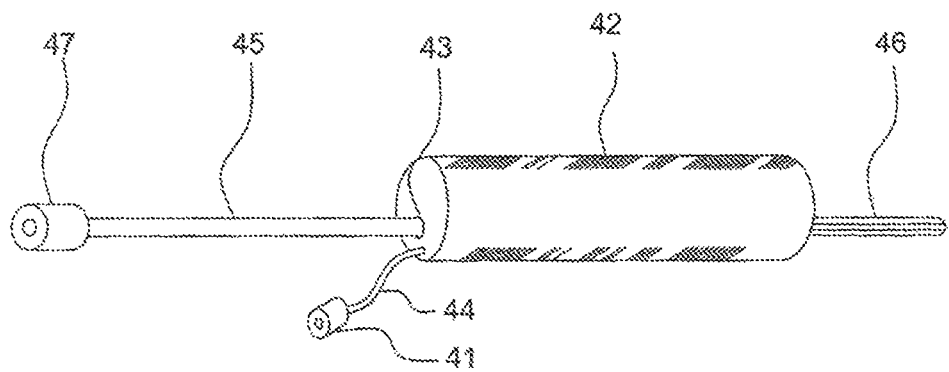

FIG. 14 Three-dimensional view of anterior nasal catheter (inflated) with deflated posterior nasal catheter passed through it.

Figure 15:
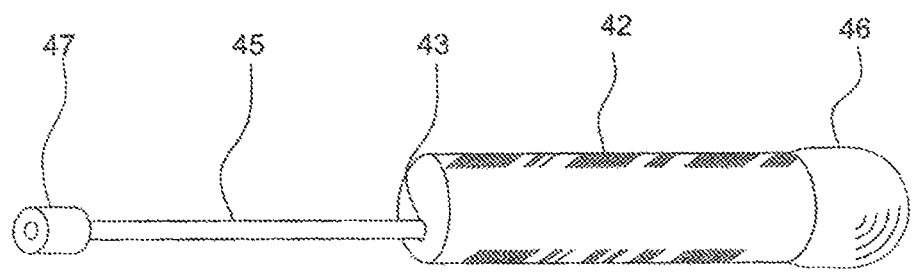

FIG. 15 Three-dimensional view of inflated posterior nasal catheter passed through inflated anterior nasal catheter.

Figure 16:
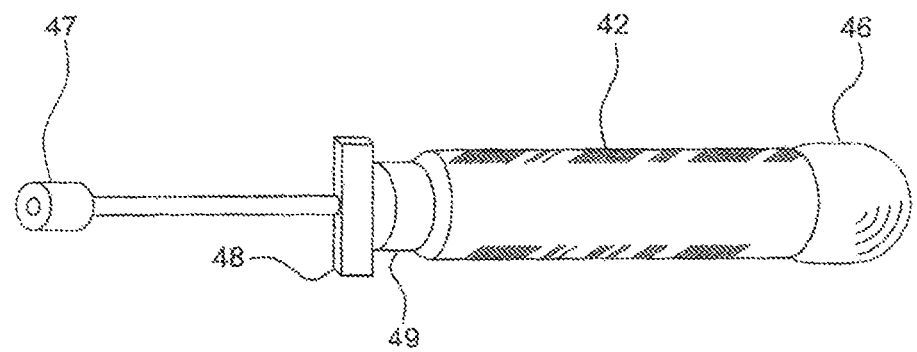

FIG. 16 Three-dimensional view of inflated anterior and posterior catheters as in FIG. 15 with clamp (48) and bolster (49) in place.

Figure 17:
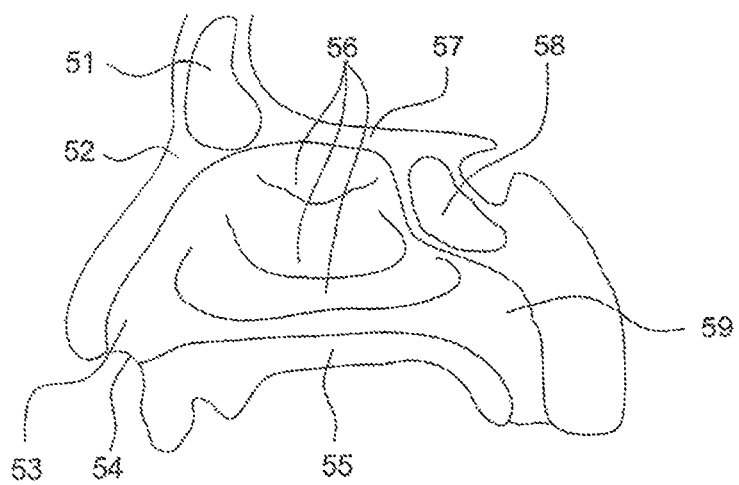

FIG. 17 Lateral view of nasal cavity and pertinent anatomy. Note that subsequent figures omit labelling of nasal structures to avoid unnecessary clutter of diagrams.

Figure 18:
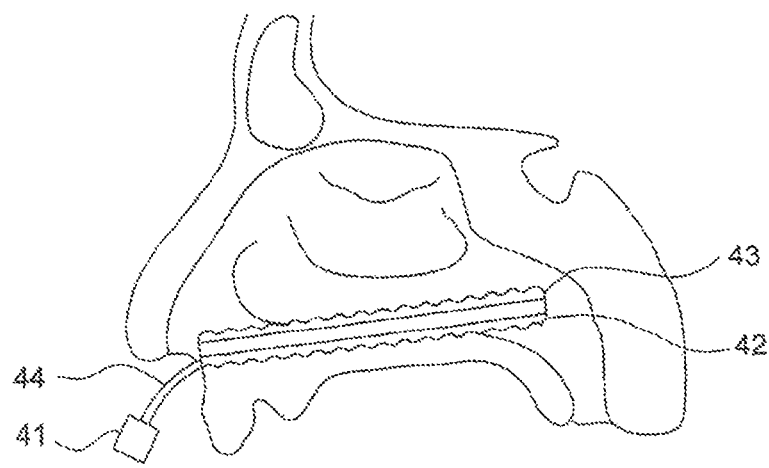

FIG. 18 Lateral view of anterior catheter in nasal cavity, deflated.

Figure 19:
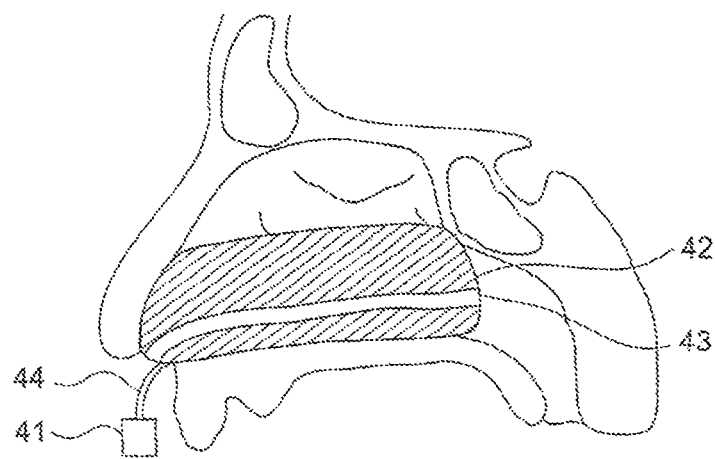

FIG. 19 Lateral view of anterior nasal catheter in nasal cavity, inflated.

Figure 20:
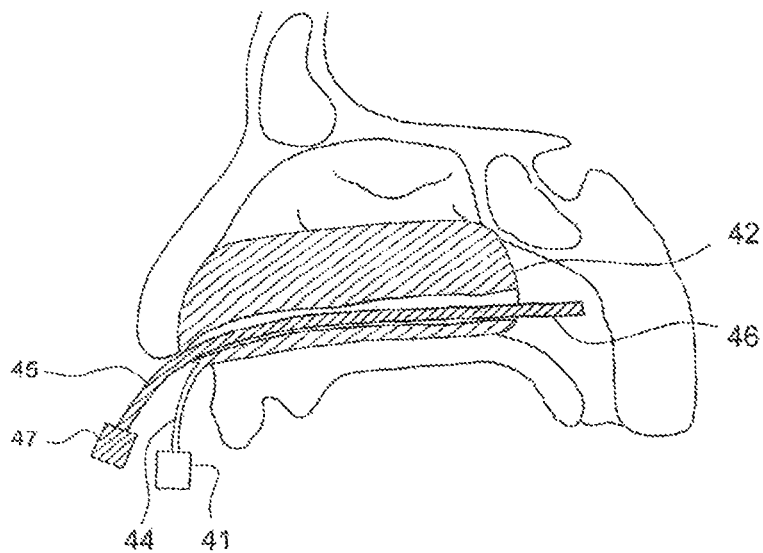

FIG. 20 Lateral view of deflated posterior nasal catheter inserted through longitudinal channel of anterior catheter (inflated).

Figure 21:
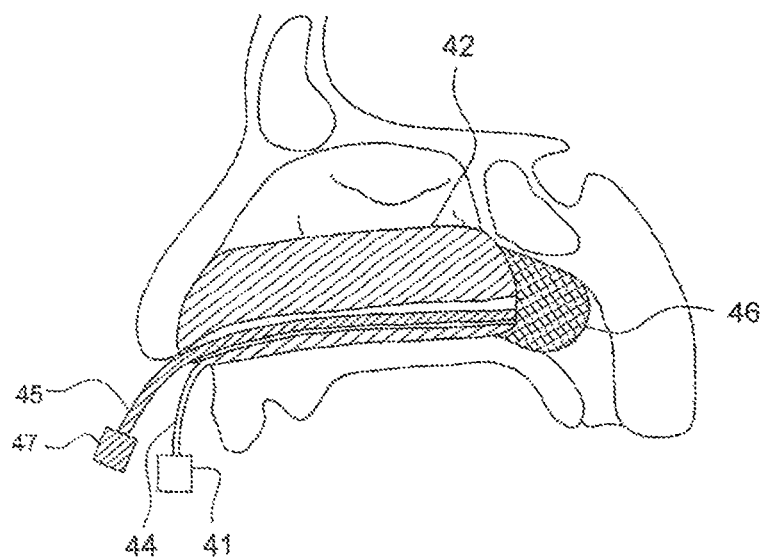

FIG. 21 Lateral view of inflated posterior nasal catheter inserted through longitudinal channel of anterior catheter (inflated).

Figure 22:
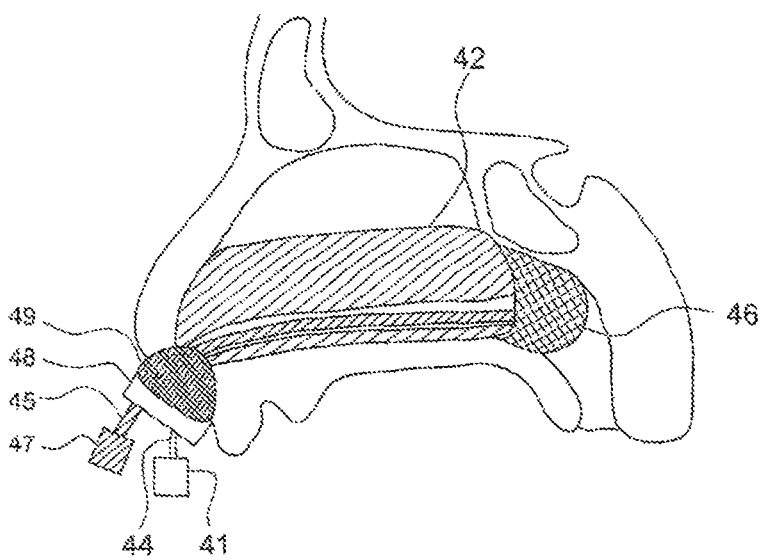

FIG. 22 Lateral view similar to FIG. 16 with bolster around shaft of posterior catheter (protecting nostril) and with clamp in place to maintain forward traction on the balloon of the posterior nasal catheter.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention provide a system, a method, and apparatus for the placement of packing in the nose to control epistaxis from any location therein. This is intended to simplify treatment by primary/urgent/emergency care physicians and other non-otolaryngologists. The present invention provides a simple and economic design that may be produced by existing manufacturing art already in practice for currently available epistaxis and medical devices. Moreover, it may be produced with different shapes of balloons and with or without a surface treatment that facilitates coagulation of blood.

As may be seen in reference to the figures above, embodiments of the present invention may include an inflatable anterior soft balloon catheter dimensioned so as to effectively conform to a patient's nasal cavity. The anterior soft balloon is connected to an inflation source via a flexible tube. A valve, such as a Luer-Lok® type syringe attachment port, may be connected to an end of the flexible tube in order to use a syringe as a source for the fluid used to inflate the balloon. This fluid may be a gas or a liquid such as water. Once inflated, the fluid is retained within the balloon by the valve.

The anterior balloon will have a generally ovoid shape along its upper, lower, and side aspects to approximate and fit the shape of the nasal cavity. In the preferred embodiment, the balloon will be non-elastic in order to provide more uniform pressure distribution throughout the nasal cavity and to reduce discomfort. The width is substantially less than the height of the balloon to improve fit. The lower portion of the balloon (beneath the longitudinal lumen) has enough vertical height to seat well along the floor of the nose.

In certain embodiments, a pilot balloon (as found on endotracheal tubes) may be provided adjacent to the valve to give the physician an external visual and tactile indication of the state of inflation of the balloon packing.

Use of the Preferred Embodiment

Illustration of the use of this device is demonstrated in FIGS. 17 to 22. FIG. 17 demonstrates pertinent nasal anatomy. The various labelled structures are not named in the remainder of drawings in order to reduce clutter.

In the event of a nosebleed, an anterior balloon pack is inserted in its deflated state into the nasal cavity. (FIG. 18) As the longitudinal lumen is not expected to support respiration it is of a smaller diameter and more flexible nature than many in prior art. This greatly facilitates passage into the nose.

FIG. 19 demonstrates the inflated pack which fills and conforms to the nasal cavity. Its soft and inelastic nature allows even distribution of pressure throughout the nasal cavity instead of focusing excessive expansion in the balloon mid-section. This treats ninety percent of nosebleeds.

Persistent hemorrhage suggests a site further back in the nose and calls for addition of posterior packing. The physician need only deflate the anterior pack enough to allow the posterior balloon passage to the nasopharynx (FIG. 20) without incurring the additional time and pain involved in its removal and replacement. After positioning the posterior pack, the physician re-inflates the forward pack.

The second balloon occludes and applies pressure to the posterior opening of the nose and the nasopharynx. The preferred embodiment uses a soft, inelastic, conforming balloon as well.

FIG. 22 demonstrates the means of maintaining forward traction on the posterior balloon. A soft bolster protects the nostril/alar area from pressure necrosis. A clamp secures the posterior balloon shaft to maintain the anterior tension. In this embodiment, it has a simple clip-like design similar to the common umbilical clamp but any other means may be substituted.

In certain embodiments, the surface of the balloons may be coated with a coagulant or hemostatic coating that would discourage bleeding upon contact with nasal tissues. Alternatively, the balloons may be encased in a mesh such as the carboxy methyl cellulose. The hemostatic coating or the mesh could be used on the anterior, posterior, or both balloon areas.

SUMMARY OF ADVANTAGES OVER PRIOR ART

The various embodiments of this invention provide solutions to a number of clinical problems associated with both patented and manufactured devices.

This proposed device may be easily produced using methods known to those skilled in the art. It offers simplified construction when compared to many designs.

Epistaxis packing remains painful to the patient and traumatic to the nasal tissues—even in the best of hands. Anything that makes the experience easier and more humane offers great clinical value. This system facilitates treatment of the ninety percent of nosebleeds which are anteriorly located plus affords simple transition to a double-balloon pack to address the remainder.

Many packs described above incorporate a rigid tube to allow some extent of nasal respiration. The functional airflow is dubious at best and the diameter and rigidity of these either prevent passage through the nasal cavity or cause it to be unduly painful and traumatic. The proposed invention lacks this questionably beneficial tube and therefore will fit more patients with enhanced comfort.

The majority of balloons use elastic material. These inflate most at their mid-sections which concentrates tissue compression in the center of the nasal cavity and away from the front where almost all nosebleeds occur. Increased pressure (with attendant pain) is often needed to overcome this problem.

The patents and products described above treat either anterior or anterior/posterior nosebleeds without ease of transitioning from one to another. Double balloon catheters have increased complexity of manufacture which is reflected with increased cost. Because of this as well as their bulkier size, it is not desirable to deploy them initially. This results in wasting of failed packs.

Treatment facilities incur additional cost by stocking a variety of packs. This proposed invention would treat virtually all nosebleeds that did not require surgical or other complex management.

It should be understood, of course, that the foregoing relates to exemplary embodiments of the invention and that modifications may be made without departing from the spirit and scope of the invention as set forth in the following claims.

What is claimed is:

1. An apparatus for controlling epistaxis, comprising:
an anterior balloon, adapted to be received in a nasal cavity of a nosebleed patient, through the patient's nostril;
an anterior inflation tube operatively connected to an anterior end of the anterior balloon;
a valve operatively connected to the anterior inflation tube to retain fluid used to inflate the anterior balloon;
an open channel extending lengthwise through the anterior balloon from a forward end to a back end of the anterior balloon,
a posterior balloon, adapted to be received in the nasopharynx of a nosebleed patient and configured when deflated to be passed through the open channel of the anterior balloon;
a flexible posterior inflation tube operatively connected to the posterior balloon;
a valve operatively connected to the posterior inflation tube to retain fluid used to inflate the posterior balloon; and
tension means to apply and maintain forward tension on the posterior inflation tube and the posterior balloon to apply adequate pressure of the posterior balloon against site(s) that may bleed at a posterior aspect of the nasal cavity, thus maintaining the posterior balloon in place, while protecting the exterior of the nostril.

2. The apparatus of claim 1, further including a hemostatic agent on the exterior of the posterior balloon.

3. The apparatus of claim 2, further including a hemostatic agent on the exterior of the anterior balloon.

4. The apparatus of claim 3, wherein said tension means includes a soft bolster at the exterior of the nostril for bearing comfortably against the nostril.

5. The apparatus of claim 4, wherein said tension means further includes a clamp secured outside the nostril, anterior of the bolster, the clamp being secured to the posterior inflation tube to maintain tension in the posterior inflation tube so that the posterior inflation tube is maintained in tension.

6. The apparatus of claim 1, wherein said tension means includes a soft bolster at the exterior of the nostril for bearing comfortably against the nostril.

7. The apparatus of claim 6, wherein said tension means further includes a clamp secured outside the nostril, anterior of the bolster, the clamp being secured to the posterior inflation tube to maintain tension in the posterior inflation tube so that the posterior inflation tube is maintained in tension.

8. An apparatus for controlling epistaxis, comprising:
- an anterior balloon, adapted to be received in a nasal cavity of a nosebleed patient, through the patient's nostril;
- an anterior inflation tube operatively connected to an anterior end of the anterior balloon;
- a valve operatively connected to the anterior inflation tube to retain fluid used to inflate the anterior balloon;
- an open channel extending lengthwise through the anterior balloon from a forward end to a back end of the anterior balloon,
- a posterior balloon, adapted to be received in the nasopharynx of a nosebleed patient and configured when deflated to be passed through the open channel of the anterior balloon;
- a flexible posterior inflation tube operatively connected to the posterior balloon;
- a valve operatively connected to the posterior inflation tube to retain fluid used to inflate the posterior balloon; and
- a hemostatic agent on the exterior of the posterior balloon.

9. The apparatus of claim 8, further including a hemostatic agent on the exterior of the anterior balloon.

\* \* \* \* \*